United States Patent [19]

Schwippert et al.

[11] Patent Number: 4,568,922
[45] Date of Patent: Feb. 4, 1986

[54] ICE DEPOSITION DETECTOR EMPLOYING IMPEDANCE CHANGE OF A VIBRATORY BODY

[75] Inventors: Gustaaf A. Schwippert, Pijnacker; Louter W. van der Kolk, Delft, both of Netherlands

[73] Assignee: Nederlandes Centrale Organisatie Voor Toegepastinatuurwetenschappelijk Ondersoek, The Haque, Netherlands

[21] Appl. No.: 514,475

[22] Filed: Jul. 18, 1983

[30] Foreign Application Priority Data

Jul. 21, 1982 [NL] Netherlands ............... 8202942

[51] Int. Cl.⁴ ............................ G08B 21/00
[52] U.S. Cl. ............................ 340/582; 307/116
[58] Field of Search ............. 340/582; 244/134 F; 261/DIG. 86; 62/140; 307/116; 310/319, 340

[56] References Cited

U.S. PATENT DOCUMENTS 3,270,330  8/1966  Weinberg ............... 340/582
4,176,524  12/1979  Kamiyama et al. ........ 340/582

Primary Examiner—Glen R. Swann, III
Attorney, Agent, or Firm—Beehler, Pavitt, Siegemund, Jagger & Martella

[57] ABSTRACT

A vibrating body is connected as one element of a voltage divider. A detector circuit is connected to the measuring point of the voltage divider. If ice is deposited on the body, its impedance changes and the resulting voltage change at the voltage divider is detected to provide an alarm or control function. The noted impedance change can be more reliably detected under a variety of conditions than the traditional vibration frequency or amplitude criteria.

9 Claims, 9 Drawing Figures

ICE DEPOSITION DETECTOR EMPLOYING IMPEDANCE CHANGE OF A VIBRATORY BODY

BACKGROUND OF THE INVENTION

1. Field of the Invention

The invention relates to an apparatus for detecting deposition on a surface, and in particular ice deposition on a cooling body, heat pump or the like.

2. State of the Prior Art

If a body has a temperature below the freezing temperature of vapour present in the ambient air, the vapour will freeze on said body. Thus the cooling body or evaporator of a refrigerating device will be covered, after some time, with an ice layer screening said body from the surroundings, which will cause the heat transfer to be substantially reduced. Therefore the cooling body is to be defrosted at regular intervals.

The longer one waits with defrosting, the longer the defrosting will last, and, moreover, the device will have operated at a lower heat-transfer efficiency during a longer period preceding the defrosting. If defrosting is initiated shortly after the beginning of the ice deposition, a relatively short defrosting period will suffice, but one should avoid, then, to disturb the temperature in the vicinity too often by defrosting.

Apparatuses for detecting ice deposition are known. In an apparatus known from GB Pat. No. 1 013 182 use is made of a vibrator adapted to be vibrated mechanically by means of an electrical vibration source, said vibrator being exposed to ice deposition, and forming itself a part of the vibration circuit. Means are present for detecting the changes in the vibration frequency of the vibrator when ice is being deposited thereon, causing the mass and, particularly, the stiffness and therefore the resonant frequency thereof to change. The change in the resonant frequency of the vibrator can be followed, and, as soon as the ice deposition limit at which defrosting should begin is reached, a signal can be derived from the frequency change by means of which means for removing the ice deposit can be switched on.

A draw-back of measuring changes in the resonant frequency is that the variation of the frequency with the thickness of the ice layer is small, and these frequencies will differ from one vibrator to an other, and, moreover, will be dependent on the temperature. This not only requires a precise adjustment of each apparatus, but also complicated compensation means for the temperature shift.

SUMMARY OF THE INVENTION

It is an object of the invention to provide such an apparatus which does not show these draw-backs. The invention is based on the discover that a change of the mass and stiffness of a vibrator not only its resonant frequency but also its impedance will change, and the impedance change with the deposition is much larger and is much less dependent on the temperature than the change in the resonant frequency, and is, therefore, much better suitable for measuring and control purposes. Such a vibrator can be considered as a parallel resonance circuit having a very large impedance at the resonance frequency, the magnitude of said maximum impedance decreasing as the resonance characteristics are changed by ice deposition.

The apparatus of the invention is characterised in that the vibration source is a sweeping oscillator having, in the active condition, a frequency which periodically varies within a range comprising the resonant frequencies of the vibrator at the prevailing deposits, in that said oscillator is connected to a voltage divider formed by a series connection of the vibrator and an impedance, and in that the means for detecting a change in the vibrations are connected to a measuring point of this voltage divider, and are adapted to detect voltage changes across a part of this voltage divider caused by impedance changes of the vibrator.

From U.S. Pat. No. 4 193 010 an apparatus is known in which a piezo-electric vibrator is energised by a sweeping oscillator, which apparatus serves to detect when a flowing substance reaches a given level, the operation of this apparatus being based on the fact that, when submerging the vibrator into the flowing substance, its vibration will be considerably damped, so that reaching said level or not will correspond to the presence or absence of a vibration. The sweeping oscillator is only used so as to allow to excite any vibrator, in spite of variations of the resonant frequencies thereof, by means of said oscillator so that the apparatus is not to be adjusted.

From DE-A No. 1 673 972 and an article of B. S. Kudsi and V. G. Ogren, "Material Presence Sensor", in IBM Techn. Discl. Bull, 15, 5 (1972, 10) 1545, apparatuses for similar purposes are known, in which a piezoelectric vibrator forms a part of the oscillator circuit.

Although the apparatus of the invention is, in the first place, intended for detecting the deposition of ice, it will be clear that this apparatus can be used anywhere where other deposits will influence the vibration behaviour of a vibrator in a similar manner.

In particular the measuring point of the voltage divider is connected to one input of a comparator stage, the other input thereof being adapted to supply thereto a dc reference voltage, said reference voltage being used for representing the maximum allowed deposit.

In a first embodiment of the apparatus of the invention, the output of the comparator stage is connected to a stage adapted to filter out the frequency of the vibration source, the output of said filter stage being connected to a stage adapted to detect the presence of pulses at this output. For the sign of the output signal of the comparator will change when the reference voltage is passed in one sense or the other, so that after filtering out the source frequency a pulse shaped signal is obtained which, however, will disappear as soon as the reference voltage is no longer passed, so that by a suitable choice of this reference signal it can be derived from the appearance or disappearance of the pulses whether the ice deposition threshold has been reached. In particular a rectifier with adjustable output voltage is inserted between the vibration source and said second input of the comparator as a reference voltage source so as to make the reference voltage independent of possible fluctuations in the voltage of the vibration source.

In a second embodiment of the apparatus of the invention, the measuring point of the voltage divider is connected to a circuit adapted for forming the envelope of the voltage in said measuring point and for determining an extreme value of said envelope, said extreme value being compared with a reference voltage, the difference between both being a measure for the output voltage of the vibrator at the resonance frequency. In particular a low-pass filter is included between the measuring point of the voltage divider and the second input of the comparator, passing the mean voltage in said measuring point.

The output circuit of the apparatus of the invention can, in particular, be formed by a pair of adjustable threshold circuits which are adapted to produce an output signal when the deposit has reached an upper or lower limit respectively.

In order to obtain a good heat transfer, the vibrator is mounted directly on the surface to be monitored, and it is favourable to choose a vibrator in which the electrode not situated at the fixed side is connected to a terminal situated at the opposite side, the whole being covered by an insulating layer in order to prevent short-circuiting by deposition of ice or the like.

BRIEF DESCRIPTION OF THE DRAWINGS

The invention will be elucidated below by reference to a drawing, showing in.

DESCRIPTION OF THE PREFERRED EMBODIMENTS

Figure 1:
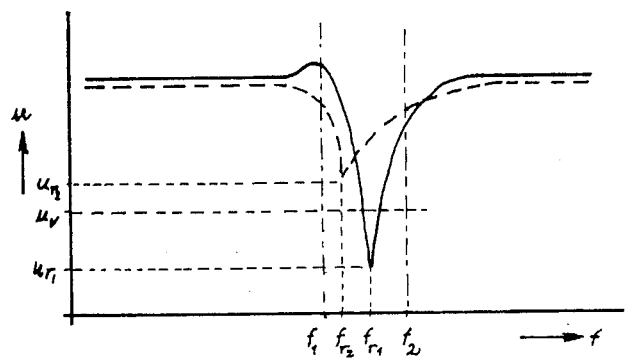
FIG. 1 a graphic representation of the vibration behaviour of a piezo-electric vibrator without and with an ice deposit.

In FIG. 1 a graphic representation of the relationship between the frequency supplied to a piezo-electric vibrator and the voltage across a series resistance of this vibrator is shown. The continuous line represents this relationship for a vibrator without an ice deposit, and the interrupted line this relationship in the case of a given ice deposit. From this graph it appears that not only the resonant frequency $f_{r1}$ and $f_{r2}$ resp. changes (i.e. decreases when ice is deposited), but that also the voltage across the series resistance at resonance will change from $u_{r1}$ to $u_{r2}$. This voltage change is much more distinct than the resonant frequency shift. Moreover it has appeared that, whereas the resonant frequency can vary with temperature, the said voltage differences are hardly influenced by temperature. This phenomenon is being utilised in the apparatus of the invention.

If, on the other hand, not the voltage across the series resistance but across the vibrator is measured, the curves of FIG. 1 will be oppositely directed.

Figure 2:
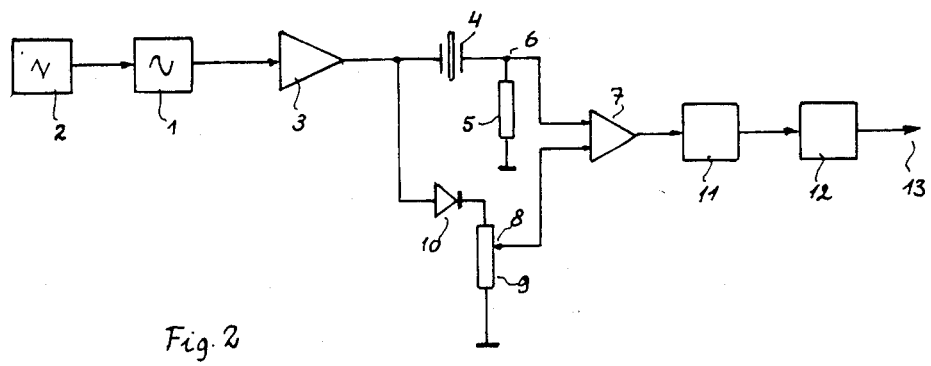
FIG. 2 a block diagram of a first embodiment of an apparatus of the invention.

The circuit diagrammatically shown in FIG. 2 comprises an oscillator 1 with variable frequency having a control input connected to a source 2 of a periodically and gradually changing voltage, e.g. a triangular voltage, so that the frequency at its output will change the frequency of the oscillator 1 periodically between the frequencies $f_1$ and $f_2$. The output of the oscillator 1 is connected, if necessary via an amplifier 3, to a piezo-electrical vibrator 4 with a series resistor 5.

The voltage across the series resistor 5 shows the behavior graphically shown in FIG. 1. The limit values $f_1$ and $f_2$ of the frequency sweep are chosen in such a manner that the resonant frequencies of the vibrator 4 within the range to be monitored will always be passed.

The connecting point 6 between the vibrator 4 and the resistor 5 is connected to one input of a comparator stage 7, the other input thereof being connected to the tap 8 of a voltage divider 9, the latter also being connected to the output of the amplifier by means of a rectifier 10.

Figure 3:
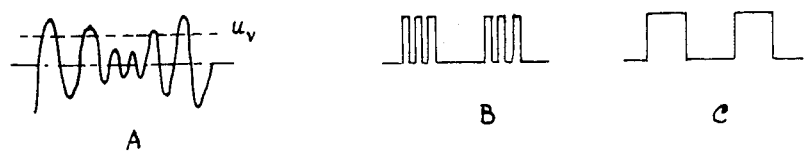
FIGS. 3A, 3B and 3C graphic representations of signal forms appearing in different points of the circuit of FIG. 2.

The signals appearing in the point 6 are shown at A in FIG. 3, the threshold voltage appearing at the tap 8 of the voltage divider 9 being indicated in FIGS. 1 and 3A by $u_y$. At B the voltages at the output of the comparator 7 are shown. As soon as the voltage across the resistor 5 decreases below the threshold voltage $u_y$, the output voltage disappears.

After the comparator a low-pass filter 11 is connected which filters out the vibration frequencies; in FIG. 3C the output signal of the is graphically represented. As long as the voltage across the resistor 5 periodically decreases below the threshold voltage, a pulse voltage of the form of FIG. 3C will be passed by the filter 11. A discriminator circuit 12 can detect the disappearance of the pulse gaps and is adapted to produce at its output 13 a control signal which, for instance, can initiate defrosting.

Figure 4:
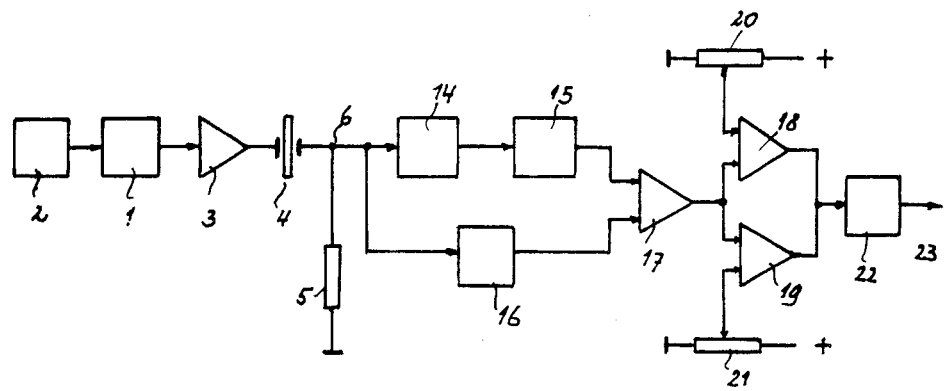
FIG. 4 a block diagram of a second embodiment of the apparatus of the invention.
Figure 5:
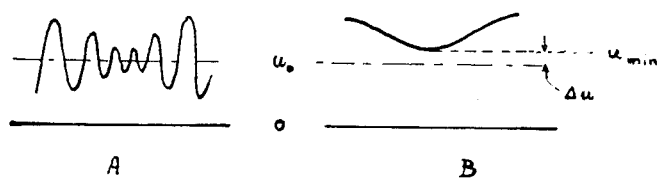
FIGS. 5A and 5B graphic representations of signal forms appearing in different points of the circuit of FIG. 4.

In FIG. 4 a corresponding diagram of another embodiment of the apparatus of the invention is shown. Herein the elements 1–5 of FIG. 2 are also included. To the point 6 a stage 14 is connected which is adapted to form the envelope of the ac voltage appearing in the point 6. This ac voltage is shown in FIG. 5A, and FIG. 5B shows the envelope of this ac voltage. To the stage 14 a minimum detector 15 is connected which can determine the minimum value $u_{min}$ indicated in FIG. 5B.

Furthermore a stage 16 which only passes the dc component of the signal in the point 6 is connected to the latter point, said component being indicated in FIGS. 5A and B by $u_o$. This stage 16 can comprise a rectifier and/or a low-pass filter. The outputs of the stages 15 and 16 are each connected to a respective input of a comparator or subtractor stage 17 by means of which the difference $\Delta u$ between the minimum value $u_{min}$ of the envelope and the value $u_o$ can be determined. It will be clear that at an increasing ice deposition the difference $\Delta u$ will increase too.

The output of the stage 17 is connected to an input of each of two comparator stages 18 and 19, the other inputs thereof being connected to a voltage divider 20 or 21 resp., which voltage dividers are connected to a source of a constant voltage. The outputs of the comparators 18 and 19 are each connected to an input of a bistable stage 22, the output 23 thereof being the control output of the apparatus. The comparator 18 is, for instance, adjusted in such a manner that, when $u_{min}$ reaches a given value corresponding to the ice deposition limit, the stage 22 is switched over, and a signal appears at the output 23 by means of which defrosting means can be switched on. The comparator 19 will, then, be adjusted in such a manner that, when reaching a value of $u_{min}$ corresponding to a given degree of defrosting, the stage 22 is switched over again and the defrosting means are switched off. By a suitable adjustment of the stages 18 and 19 by means of the voltage dividers 20 and 22 resp. it is possible to obtain that switching on and off will not take place too repeatedly, as would be the case when using one single threshold value.

It will be clear that a similar manner of controlling the defrosting means can be used also in the circuit of FIG. 2, and then the length of the pulse gaps can be transformed into corresponding voltages to be supplied to the comparators 18 and 19 of FIG. 4.

Figure 6:
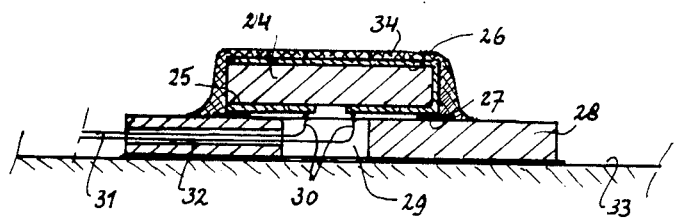
FIG. 6 a diagrammatic cross-section of an embodiment of a piezo-electric vibrator for an apparatus of the invention.

FIG. 6 shows a diagrammatical cross-section of a practical embodiment of a piezo-electric vibrator suitable for the present apparatus. This vibrator comprises a crystal plate 24 with at each side an electrode 25 and 26 resp., the upper electrode 26 being bent around the plate and ending at the lower side at some distance from the electrode 25. The crystal plate is mounted by means of an insulating ring 27 on a steel plate 28, the latter being provided, in the central part, with an opening 29. In this opening the terminals 30 of the electrodes 25 and 26 are situated, and the conductors 31 connected to these terminals are led outwards through a bore 32 in the metal plate 28. This metal plate 28 is attached in a suitable point on the surface 33 to be monitored by means of a good heat contact. In order to avoid short-circuits by moisture deposition, the crystal plate 24 with the electrodes 25 and 26 is covered by an insulating layer 34.

It will be clear that within the scope of the invention many modifications are possible. For instance the used vibrators can be designed in many other ways, and instead of piezo-electric vibrators also magneto- or electrostrictive or also electro-mechanical vibrators can be used.

Also the used electrical circuits can be designed in many other ways, and, in particular, the series resistor 5 shown can be replaced by an other impedance which, in particular, can be a part of the sweeping oscillator 1, provided that from the voltage divider thus obtained a voltage can be derived which allows to detect the changes in the deposit.

What is claimed is:

1. An apparatus for detecting deposition of ice or the like, comprising a vibrator adapted to be caused to vibrate by means of an electrical vibration source, a surface of said vibrator being adapted to be exposed to the deposition, means for detecting changes in the vibration of said vibrator when deposition takes place, and an output circuit for producing an output signal when the deposit has exceeded a given limit, characterized in that the vibration source is a sweeping oscillator (1, 2) having, in the active condition, a frequency which periodically varies within a range comprising the resonant frequencies of the vibrator (4) at the prevailing deposits, in that said oscillator (1, 2) is connected to a voltage divider formed by a series connection of the vibrator (4) and an impedance (5), and in that the means for detecting a change in the vibration (7–12; 14–23) are connected to a measuring point (6) of this voltage divider (4, 5), and are adapted to detect voltage changes across a part of this voltage divider caused by impedance changes of the vibrator (4).

2. The apparatus of claim 1, characterised in that the measuring point (6) of the voltage divider (4, 5) is connected to one input of a comparator stage (7; 17), the other input thereof being adapted to supply thereto a reference voltage.

3. The apparatus of claim 2, characterised in that the output of the comparator stage (7) is connected to a stage (11) adapted to filter out the frequency of the vibration source, and that the output of said filter stage (11) is connected to a stage (12) adapted to detect the presence of pulses at this output.

4. The apparatus of claim 2 or 3, characterised in that between the vibration source (1, 2) and the second input of the comparator stage (7), a rectifier with variable output voltage (8, 9, 10) is inserted as a reference voltage source.

5. The apparatus of claim 2, characterised in that the measuring point (6) of the voltage divider (4, 5) is connected to a circuit (14, 15) for forming the envelope of the voltage in the measuring point (6) and determining an extreme value of said envelope.

6. The apparatus of claim 5, characterised in that between the measuring point (6) and the second input of the comparator (17) a low-pass filter (16) is connected, passing the mean voltage in the measuring point (6).

7. The apparatus of claim 1 characterised in that the output circuit is formed by two adjustable threshold circuits (18, 20; 19, 21), adapted to produce an output signal when the deposit has reached an upper or lower limit respectively.

8. The apparatus of claim 1, said vibrator comprising a vibrator plate provided with an electrode on each side, which plate is adapted to be mounted with one side fixed in good heat contact on a surface to be monitored, characterised in that the electrode (26) on the not-fixed side of the plate (24) is connected to a connecting point (30) at the other side, which connecting point and the connecting point (30) of the other electrode (25) are situated in a cavity (29) of an intermediate body (28) of a good heat conducting material and situated between the vibrator plate (24) and the surface to be monitored (33).

9. The apparatus of claim 8, characterised in that the crystal plate (24) is covered by an insulating layer (27).

* * * * *

UNITED STATES PATENT AND TRADEMARK OFFICE
CERTIFICATE OF CORRECTION

PATENT NO.   : 4,568,922
DATED        : February 4, 1986
INVENTOR(S)  : Gustaaf A. Schwippert; Louter W. van der Kolk It is certified that error appears in the above-identified patent and that said Letters Patent are hereby corrected as shown below:

On the title page, Item [73] should read:

Assignee: Nederlandse Centrale Organisatie Voor Toegepast-Natuurwetenschappelijk Onderzoek, The Hague

Signed and Sealed this

Sixteenth Day of December, 1986

*Attest:*

DONALD J. QUIGG

*Attesting Officer*     *Commissioner of Patents and Trademarks*